US011633520B2

(12) United States Patent
Cornwell et al.

(10) Patent No.: US 11,633,520 B2
(45) Date of Patent: Apr. 25, 2023

(54) PERFORATED TISSUE GRAFT

(71) Applicant: TEI Biosciences, Inc., Boston, MA (US)

(72) Inventors: Kevin Cornwell, Holliston, MA (US); Kenneth James, Barton, VT (US)

(73) Assignee: TEI BIOSCIENCES, INC., Boston, MA (US)

( * ) Notice: Subject to any disclaimer, the term of this patent is extended or adjusted under 35 U.S.C. 154(b) by 0 days.

(21) Appl. No.: 15/913,152

(22) Filed: Mar. 6, 2018

(65) Prior Publication Data
US 2018/0250441 A1  Sep. 6, 2018

Related U.S. Application Data

(60) Provisional application No. 62/467,503, filed on Mar. 6, 2017.

(51) Int. Cl.
| | | |
|---|---|---|
| *A61L 27/36* | (2006.01) | |
| *A61K 35/34* | (2015.01) | |
| *A61K 35/44* | (2015.01) | |
| *C12N 5/00* | (2006.01) | |
| *A61L 27/56* | (2006.01) | |
| *A61K 35/36* | (2015.01) | |
| *C12N 5/077* | (2010.01) | |

(52) U.S. Cl.
CPC .......... *A61L 27/3604* (2013.01); *A61K 35/34* (2013.01); *A61K 35/36* (2013.01); *A61K 35/44* (2013.01); *A61L 27/3691* (2013.01); *A61L 27/56* (2013.01); *C12N 5/0068* (2013.01); *A61L 27/3687* (2013.01); *A61L 2430/40* (2013.01); *C12N 5/0652* (2013.01); *C12N 2533/54* (2013.01); *C12N 2533/56* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,326,356 A | 7/1994 | Della Valle et al. | |
| 5,650,164 A | 7/1997 | Della Valle et al. | |
| 5,658,331 A | 8/1997 | Della Valle et al. | |
| 5,665,391 A * | 9/1997 | Lea | A61F 2/105 424/400 |
| 5,755,791 A | 5/1998 | Whitson et al. | |
| 5,955,110 A | 9/1999 | Patel et al. | |
| 5,968,096 A | 10/1999 | Whitson et al. | |
| 5,997,575 A | 12/1999 | Whitson et al. | |
| 6,197,036 B1 | 3/2001 | Tripp et al. | |
| 6,206,931 B1 | 3/2001 | Cook et al. | |
| 6,398,819 B1 | 6/2002 | Bell | |
| 6,409,764 B1 | 6/2002 | White et al. | |
| 6,666,892 B2 | 12/2003 | Hiles et al. | |
| 6,696,074 B2 | 2/2004 | Dai et al. | |
| 6,969,523 B1 | 11/2005 | Mattern et al. | |
| 7,244,444 B2 | 7/2007 | Bates | |
| 7,354,702 B2 | 4/2008 | Dai et al. | |
| 7,358,284 B2 | 4/2008 | Griffey et al. | |
| 7,652,077 B2 | 1/2010 | Cook et al. | |
| 7,699,895 B2 | 4/2010 | Hiles et al. | |
| 7,713,552 B2 | 5/2010 | Bleyer et al. | |
| 7,723,108 B2 | 5/2010 | Truncale et al. | |
| 7,745,217 B2 | 6/2010 | Patel et al. | |
| 7,959,554 B2 | 6/2011 | McAlexander et al. | |
| 8,007,542 B2 | 8/2011 | Hiles et al. | |
| 8,049,059 B2 | 11/2011 | Bleyer et al. | |
| 8,067,149 B2 | 11/2011 | Livesey et al. | |
| 8,128,708 B2 | 3/2012 | Hiles et al. | |
| 8,192,763 B2 | 6/2012 | Johnson | |
| 8,323,701 B2 | 12/2012 | Daniel et al. | |
| 8,415,159 B2 | 4/2013 | Ward et al. | |
| 8,460,691 B2 | 6/2013 | Lauilzen et al. | |
| 8,557,581 B2 | 10/2013 | Ngo et al. | |
| 8,591,930 B2 | 11/2013 | Hiles et al. | |
| 8,716,227 B2 | 5/2014 | Cook et al. | |

(Continued)

FOREIGN PATENT DOCUMENTS

| | | | |
|---|---|---|---|
| DE | 102010023413 A1 | 12/2011 | |
| EP | 2845612 A1 | 3/2015 | |

(Continued)

OTHER PUBLICATIONS

Acelity Alloderm Select Duo Product Press Release, Oct. 21, 2016.
Northeastern Society of Plastic Surgeons 2014 Annual Meeting Abstract.
Xiao et al. "The Role of Pores on Acellular Dermal Matrix Substitute" Annals of Burns and Fire Disasters—vol. XIX—n. 4—Dec. 2006.
Dieterich et al. "Biological Matrices and Synthetic Meshes Used in Implant-based Breast Reconstruction—a Review of Products Available in Germany", Geburtsh Frauenheilk 2013; 73: 1100-1106.
Bard Davol Collamend Product Brochure, Dec. 31, 2009.
Cook Medical Biodesign Product Brochure, Sep. 2016.
Integra Meshed Bilayer Wound Matrix Brochure, Dec. 31, 2010.
Integra Meshed Dermal Regeneration Template Brochure, Dec. 31, 2014.
Integra PriMatrix Product Brochure, Dec. 31, 2016.

(Continued)

*Primary Examiner* — Nghi V Nguyen
(74) *Attorney, Agent, or Firm* — KDW Firm PLLC

(57) ABSTRACT

A tissue graft for soft tissue repair or reconstruction comprising a sheet of a biopolymer-based matrix having a plurality of small perforations and a plurality of large perforations. The small perforations are sized to facilitate clotting and granulation tissue development within the perforations which, in turn, facilitates revascularization and cell repopulation in the patient. The large perforations are sized to reduce the occurrence of clotting and granulation tissue development within the perforations so that extravascular tissue fluids accumulating at the implant site can drain through the tissue graft. The large perforations enhance mammal tissue anchoring by permitting mammal tissue to compress into the perforations increasing mammal tissue contact area.

23 Claims, 2 Drawing Sheets

(56) References Cited

U.S. PATENT DOCUMENTS

| | | | |
|---|---|---|---|
| 8,784,499 | B2 | 7/2014 | Owens et al. |
| 8,795,384 | B2 | 8/2014 | Nelson et al. |
| 8,808,392 | B2 | 8/2014 | Cook et al. |
| 8,882,850 | B2 | 11/2014 | Hiles et al. |
| 8,883,210 | B1 | 11/2014 | Fruncale et al. |
| 8,920,515 | B2 | 12/2014 | Cook et al. |
| 8,986,377 | B2 | 3/2015 | Richter et al. |
| 8,998,974 | B2 | 4/2015 | Carlson et al. |
| 9,011,895 | B2 | 4/2015 | Dai et al. |
| 9,044,455 | B2 | 6/2015 | Shah et al. |
| 9,144,634 | B2 | 9/2015 | Stopek et al. |
| 9,220,259 | B2 | 12/2015 | Owens et al. |
| 9,295,757 | B2 | 3/2016 | Patel et al. |
| 9,375,513 | B2 | 6/2016 | Sun et al. |
| 9,382,422 | B2 | 7/2016 | Owens et al. |
| 9,486,316 | B2 | 11/2016 | Horton et al. |
| 9,532,866 | B2 | 1/2017 | Kim et al. |
| 9,533,011 | B2 | 1/2017 | Daniel et al. |
| 9,549,812 | B2 | 1/2017 | Shetty et al. |
| 10,039,633 | B2 | 8/2018 | Ansorge et al. |
| 2004/0034374 | A1 | 2/2004 | Zatzsch et al. |
| 2008/0097601 | A1 | 4/2008 | Codori-Hurff et al. |
| 2010/0075419 | A1 | 3/2010 | Inagaki et al. |
| 2010/0303886 | A1 | 12/2010 | Janis |
| 2011/0070284 | A1 | 3/2011 | Depaula et al. |
| 2011/0293666 | A1* | 12/2011 | Wang ................. A61L 27/3633 424/400 |
| 2014/0315847 | A1 | 10/2014 | Peck et al. |
| 2015/0157451 | A1 | 6/2015 | Bowley et al. |
| 2015/0366669 | A1* | 12/2015 | Bartee .................... A61L 27/18 623/23.5 |
| 2016/0045296 | A1 | 2/2016 | Guo |
| 2016/0206784 | A1 | 7/2016 | Jessop et al. |
| 2016/0206785 | A1 | 7/2016 | Patel et al. |
| 2017/0021058 | A1* | 1/2017 | Huang ................ A61L 27/3604 |

FOREIGN PATENT DOCUMENTS

| | | | |
|---|---|---|---|
| IT | 0000283625 | 4/2015 | |
| JP | 2008-104866 | 5/2008 | |
| JP | 2013-503696 | 2/2013 | |
| JP | 2016-536315 | 11/2016 | |
| WO | 1997/06837 A1 | 2/1997 | |
| WO | WO97/06837 | 2/1997 | |
| WO | WO-9706837 A1 * | 2/1997 | ............ A61F 2/105 |
| WO | WO01/80774 | 11/2001 | |
| WO | WO2010/052584 | 5/2010 | |
| WO | WO-2010052584 A2 * | 5/2010 | ........... A61F 2/0045 |
| WO | 2011031642 A2 | 3/2011 | |
| WO | WO2011/028521 | 3/2011 | |
| WO | 2013106556 A2 | 7/2013 | |
| WO | 2014144188 A1 | 9/2014 | |
| WO | 2014160008 A1 | 10/2014 | |
| WO | 2015065923 A1 | 5/2015 | |
| WO | WO2015/066668 | 5/2015 | |
| WO | 2016081386 A1 | 5/2016 | |
| WO | WO2016-118558 | 7/2016 | |
| WO | 2016/130559 A1 | 8/2016 | |

OTHER PUBLICATIONS

Integra SurgiMend PRS and PRS Meshed product brochure, Dec. 31, 2017.
LifeCell Strattice Perforated Product Brochure, Dec. 31, 2016.
Musculoskeletal Transplant Foundation (MTF) Catalog—FlexHD pliable perforated products on p. 64, Dec. 31, 2012.
RTI Surgical Tutopatch and Tutomesh Product Brochure, Dec. 31, 2014.
English translation of Japanese Office Action for Application No. 2019-548300 dated Jan. 21, 2020.
English translation of Japanese Office Action for Application No. 2019-548300 dated Apr. 9, 2020.
European Search Report dated Nov. 26, 2020 for EP Application No. 18764351.5.

* cited by examiner

PERFORATED TISSUE GRAFT

RELATED APPLICATION DATA

This application claims the benefit of U.S. provisional application Ser. No. 62/467,503 filed Mar. 6, 2017, hereby incorporated by reference herein in its entirety.

BACKGROUND

The present invention relates to the field of tissue engineering, and in particular to animal-derived, bioremodelable, biopolymer scaffold materials used to repair animal tissue.

In the field of tissue engineering, the following three components are used alone or in combination to repair or create new tissue and organ substitutes: 1) scaffolds made of naturally-occurring polymers (e.g. collagens), man-made polymers, (e.g. PTFE, Dacron, PET or polyethylene) or self-degrading, man-made polymers (e.g. PLA or PGA); 2) signaling molecules that give developmental instructions to cells; and 3) cells.

Man-made implant materials such as synthetic polymers, plastics, and surface-coated metals may have different degrees of immunogenicity and suffer from significant limitations that prohibit their broad applications. A major limitation is that cells cannot remodel them after implantation. They may be susceptible to microbial infection, and some undergo calcification.

Decellularized animal tissues comprise scaffolds made of naturally-occurring polymer. Decellularized animal tissues and decellularization processes are described in U.S. Pat. Nos. 9,011,895, 7,354,702, and 6,696,074, each of which is hereby incorporated by reference in its entirety. The patents describe methods of forming and preserving a bioremodelable, biopolymer scaffold material by subjecting animal tissue, for example fetal or neo-natal bovine dermis tissue, to chemical and mechanical processing. The resulting product is characterized by its microbial, fungal, viral and prion inactivated state, and it is strong, bioremodelable, drapable and does not undergo calcification. Such decellularized animal tissues have broad applicability in clinical applications. PRIMATRIX Dermal Repair Scaffold and SURGIMEND Collagen Matrix (TEI Biosciences, Inc., Waltham, Mass.) are examples of decellularized animal tissues on the market.

Holes or gaps have been placed in tissue grafts to allow fluid drainage, substance or cell passage, and/or graft material expansion. For example, PRIMATRIX Dermal Repair Scaffolds are offered on the market in meshed and fenestrated configurations in addition to the solid configuration.

Although various tissue graft materials are available commercially, there remains a need for tissue grafts that have improved physical properties and effectiveness for tissue repair, regeneration, and reconstruction.

SUMMARY

Briefly and in general terms, the present invention provides tissue grafts such as decellularized tissue products having perforations of at least two different sizes. The introduction of perforations of selected sizes in decellularized tissue products modulates the biologic properties of the implant. More specifically, the size of the perforation affects local fluid collection/removal, revascularization, tissue generation, and tissue remodeling characteristics.

In accordance with an aspect of the present invention, a tissue graft for repair or reconstruction of tissue of a mammal is provided. The tissue graft comprises a sheet of a biopolymer-based matrix having a plurality of small perforations and a plurality of large perforations, wherein the small perforations are smaller in size than the large perforations. The creation of specific hole patterns within the tissue graft directs different biological responses by location within the device. Surgical site fluid drainage, tissue regeneration and wound healing is controlled by altering the size, and location of perforations in the tissue graft.

In accordance with another aspect of the present invention, there is provided a method for repair or reconstruction of soft tissue by applying a tissue graft to a patient in need of the treatment, wherein the tissue graft has a specific hole pattern that directs different biological responses within the device. More specifically, the method of repairing or constructing tissue in a patient, comprises providing a tissue graft comprising a sheet of a tissue graft material and having a plurality of small perforations and a plurality of large perforations, wherein the small perforations are smaller in size than the large perforations; applying the tissue graft to the patient at an implant site; allowing revascularization and cell repopulation in the patient; and applying surgical drains or negative pressure wound therapy to remove extravascular tissue fluids from the implant site in the perioperative and early postoperative period.

Other features and advantages of the present invention will become more apparent from the following detailed description of the invention, when taken in conjunction with the accompanying exemplary drawings.

BRIEF DESCRIPTION OF THE DRAWINGS

Embodiments of the present invention are described herein with reference to the drawings, in which.

DETAILED DESCRIPTION OF CERTAIN EXEMPLARY EMBODIMENTS

Figure 1:
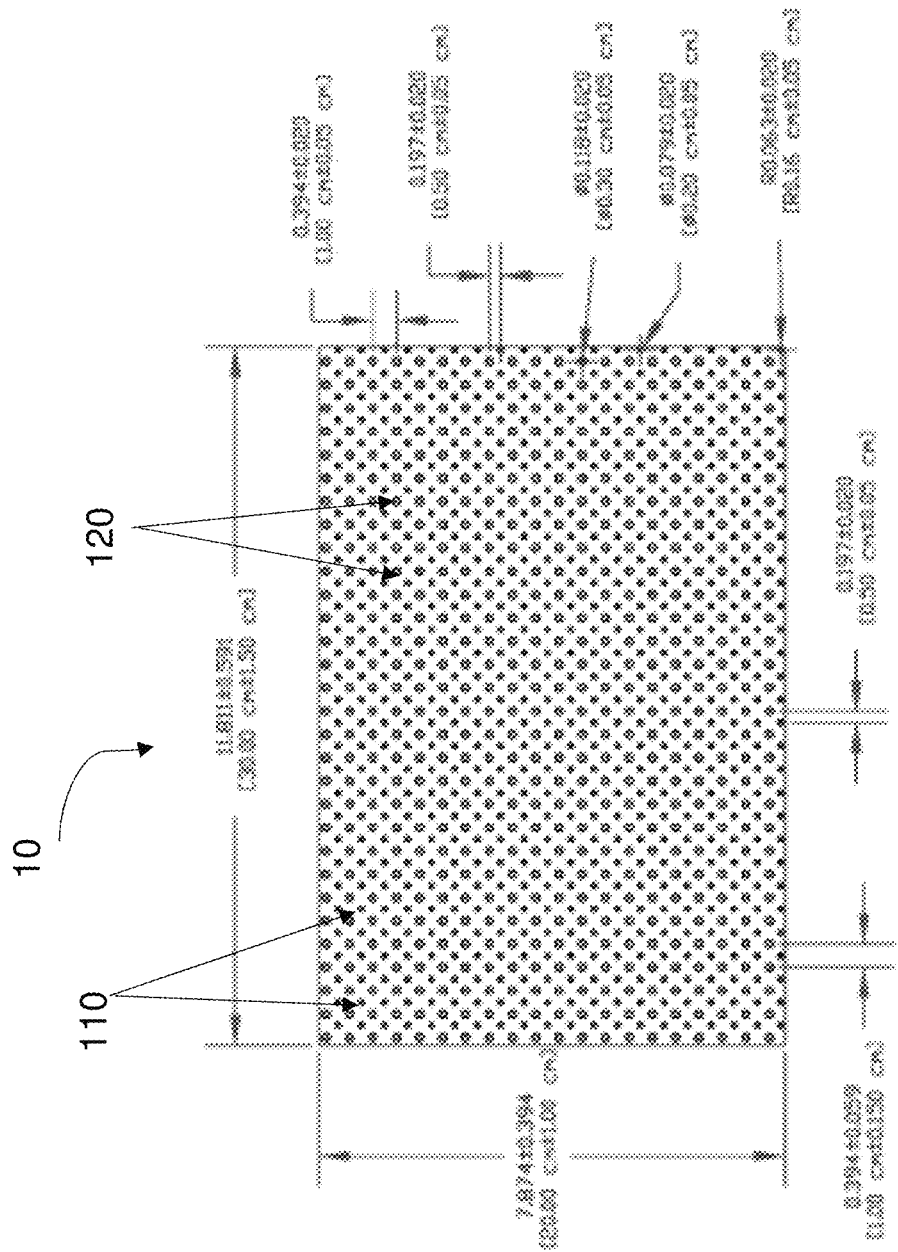
FIG. 1 is a top plan view of an embodiment of a tissue graft in accordance with the present invention.

The present disclosure relates to tissue grafts having perforations of at least two different sizes for repair or reconstruction of soft tissue. Embodiments of the presently disclosed tissue grafts will be described in detail with reference to the drawings.

The terms "tissue graft" and "tissue graft material" as used herein refer to an implant or repair material derived from tissue, including autograft, allograft or xenograft tissues, materials engineered from materials originated from human or animal tissue, and combinations of the foregoing. Examples of tissue grafts and tissue graft materials include decellularized animal tissue, engineered collagen matrices, and human placental tissue.

The term "perforation" as used herein refers to an aperture passing through something, or an act of making an aperture on something. A perforation can be of any shape or size. The terms "perforation", "opening", "hole", "gap", "void", "pore", and "aperture" may be used herein interchangeably.

The term "sheet" as used herein refers to a broad, relatively thin, surface or layer of a material. Such sheets may be flat or uniform in thickness or may vary in thickness across their surfaces and may be of any shape.

As used herein, transitional phrases such as "comprising", "including", "having", "containing", "involving", "composed of", and the like are to be understood to be open-ended and to mean including but not limited to.

The indefinite articles "a" and "an", as used herein in the specification and in the claims, unless clearly indicated to the contrary, should be understood to mean "at least one".

The term "about" as used herein indicates that a value can vary by up to ±10%, for example, ±5%, ±2% or ±1%.

In accordance with an aspect of the present invention, a tissue graft is provided that comprises a sheet of a tissue graft material having a plurality of small perforations and a plurality of large perforations, wherein the small perforations are smaller in size than the large perforations.

The tissue graft material may be an acellular collagen matrix derived from fetal or neonatal bovine dermis. A sheet of a naturally occurring, biopolymer-based matrix may be produced from animal tissue by a process comprising the following steps: (1) removing the tissue from its animal source and then removing the flesh from the tissue; (2) optionally extracting growth and differentiation factors from the tissue; (3) inactivating infective agents of the tissue, for example, by treating with NaOH; (4) mechanically applying pressure to remove undesirable components from the tissue; (5) washing the tissue for removal of chemical residues; (6) optionally drying, for example, lyophilizing; and (7) optionally cross-linking the tissue after chemical and mechanical treatment; (8) optionally cutting the tissue into desired shapes and sizes; and (9) optionally terminally sterilizing. See, for example, U.S. Pat. No. 9,011,895, which is incorporated herein by reference in its entirety. To produce the tissue graft of the present invention, an additional step is included in the process to add particularly sized perforations during the process, for example, after the drying step, after the cross-linking step, or after the cutting step. The perforating step will be described in more detail below.

Another example of a tissue graft material is an engineered collagen matrix. A sheet of an engineered collagen matrix may be produced from a process comprising the steps: (1) preparing a dispersion of collagen (for example, bovine tendon collagen); (2) optionally adding glycosaminoglycan (GAG) to the collagen dispersion; (3) lyophilizing the collagen or collagen/GAG dispersion to dryness; (4) optionally applying a silicone layer to the lyophilized collagen or collagen/GAG material; (5) optionally cross-linking the lyophilized collagen or collagen/GAG material; (6) optionally cutting the tissue into desired shapes and sizes; and (7) optionally terminally sterilizing. See, for example, U.S. Pat. No. 6,969,523, which is incorporated herein by reference in its entirety. To produce the tissue graft of the present invention, an additional step is included in the process to add particularly sized perforations during the process, for example, after the lyophilizing step, after the applying a silicone layer step, after the cross-linking step, or after the cutting step. The perforating step will be described in more detail below.

It should also be understood that, unless clearly indicated to the contrary, in any process or methods described or claimed herein that include more than one step or act, the order of the steps or acts of the method is not necessarily limited to the order in which the steps or acts of the method are recited. The order of steps or acts may be adjusted by those skilled in the art.

FIG. 1 depicts an exemplary embodiment of a tissue graft of the present invention. The tissue graft 10 comprises a sheet of a tissue graft material, for example, acellular dermis from fetal and neonatal bovine tissue, having a plurality of small perforations 110 and a plurality of large perforations 120. The small perforations 110 are smaller in size than the large perforations 120. The small and large perforations are circular or substantially circular. The small perforations have a diameter of about 2 mm and speed surgical mesh revascularization and cell repopulation. The large perforations have a diameter of about 3 mm and improve tissue anchoring by permitting patient muscle tissue to compress into the perforations of larger diameter, thus allowing increased contact area, and more rapid attachment or sealing to potentially reduce seroma. The tissue graft of the embodiment is about 2 mm thick. The small perforations of about 2 mm in diameter have an open area of 3.14 $mm^2$ and a void volume of about 6.28 $mm^3$. The large perforations of about 3 mm in diameter have an open area of 7.07 $mm^2$ and a void volume of about 14.14 $mm^3$. The tissue graft including perforations of two sizes permits drainage/removal of tissue fluids produced as a result of local tissue trauma.

The tissue graft may have a thickness in the range of about 0.5 mm to about 4.5 mm and preferably in the range of about 2 mm to about 4 mm.

The small perforations may be about 1 mm to about 2.5 mm in diameter, and the large perforations may be about 2.5 mm to about 4 mm in diameter. The small perforations and the large perforations have diameters in the ratio of about 1:1.2 to about 1:2 and preferably about 1:1.3 to about 1:1.7, for example about 1:1.5.

Although the embodiment depicted in the drawing has circular perforations, it is contemplated that the perforations can have any shape, such as oval, square, rectangular, diamond or any irregular or other shape. The small perforations and the large perforations have open areas in the ratio of about 1:1.5 to about 1:3, and preferably about 1:2 to about 1:2.5, for example about 1:2.25. The small perforations and the large perforations have void volumes in the ratio of about 1:1.5 to about 1:3, and preferably about 1:2 to about 1:2.5, for example about 1:2.25.

The small perforations are sized to facilitate fibrin provisional matrix formation (clotting) and granulation tissue development within the perforations which, in turn, is a source of blood vessels and cells to facilitate revascularization and cell repopulation of the tissue graft implanted on the mammal. The large perforations are sized to reduce the occurrence of fibrin provisional matrix formation and granulation tissue development within the perforations so that extravascular tissue fluids accumulating at an implant site in the mammal can readily drain through the tissue graft and be removed from the implant site in the perioperative and early postoperative period via surgical drains or negative pressure wound therapy. The large perforations are sized to enhance mammal tissue anchoring by permitting mammal tissue to compress into the perforations increasing mammal tissue contact area.

The small and large perforations are arrayed in rows, and the rows are substantially parallel to each other. The tissue graft may have a plurality of rows of small perforations and a plurality of rows of large perforations, and the rows of small perforations alternate with the rows of large perforations. The large perforations and small perforations are distributed in staggered rows and columns such that one small perforation is centered about every four adjacent large perforations arranged in a substantially square or rectangular manner, and one large protrusion is centered about every four adjacent small protrusions arranged in a substantially square or rectangular manner.

According to one aspect, the plurality of rows of small and large perforations are equally spaced substantially on the entire surface of the tissue graft. The small perforations are spaced about 5 mm to about 20 mm apart, and preferably about 7 mm to about 15 mm apart, for example, about 10 mm apart, as measured between the centers of two adjacent perforations, for example in the same row. The large perforations are spaced about 5 mm to about 20 mm apart, and preferably about 7 mm to about 15 mm apart, for example, about 10 mm apart, as measured between the centers of two adjacent perforations, for example in the same row. It is anticipated that there may be applications where the small and/or large perforations are desired for only certain portions of the tissue graft. For example, the plurality of small and large perforations are distributed over about 75%, over about 50%, or over about 25% of the surface of the tissue graft. In addition, the perforations of the same size do not need to be arranged in a row. For example, the large perforations may be grouped in certain areas while the small perforations may be grouped in other areas, and these large perforation areas and small perforation areas may be evenly distributed on the entire or partial surface of the tissue graft or in any other arrangement depending on the clinical applications and desired results.

The row of small perforations and the row of large perforations are spaced about 5 mm to about 20 mm apart, and preferably about 7 mm to about 15 mm apart, for example, about 10 mm apart, as measured between a first line connecting the centers of two adjacent small perforations in the row and a second line connecting the centers of two adjacent large perforations in the row.

Perforation of the tissue graft is performed using a perforation machine that comprises a cutting die having a surface of desired dimensions. The cutting die has on its surface punches that have shapes and sizes that correspond to the predetermined shapes and sizes of the perforations on the tissue graft to be prepared. The punches are distributed in a pattern that corresponds to the predetermined perforation pattern of the tissue graft to be prepared. Suitable perforation machines include those for industrial use.

While holes, gaps, or voids have been placed in decellularized tissues previously, the holes in the prior art are all the same size and often spaced very far apart to allow fluid drainage while minimization the effect on mechanical properties of the mesh. In the present invention, the differential biological effects of hole sizes have been identified and utilized to direct revascularization, tissue generation, and tissue engineering. The creation of specific hole patterns within a device to direct these responses differentially by location within the device is a significant difference from the prior art.

The present invention provides the ability to control surgical site fluid drainage, tissue regeneration and wound healing by altering the size and/or location of perforations in a surgical mesh. It provides the ability to control blood flow into a newly generated tissue.

The introduction of holes and void spaces into tissue grafts modulates the biologic properties of the implant with different size gaps or holes affecting the revascularization, tissue generation, and tissue remodeling characteristics. Once implanted, these designed voids are found to be filled with host generated tissue. Where the cell, vascular density, and metabolic/nutritional demand in the host generated tissue within the voids is greater than that generated within the microporosity of implanted extracellular matrix (ECM), a macro/microvasculature is observed to form that is directed specifically towards these fabricated voids in the implant. Strategically placing such voids (holes, fenestrations/slits, and/or grooves) is thus a mechanism to induce directed angiogenesis of a macro/microvasculature. Directed angiogenesis can be used in tissue engineering and reconstructive surgery to spatially regulate the flow of blood and blood constituents throughout a newly generated tissue, to direct macro/microvasculature towards host-generated capillary networks found to fill the previously fabricated tissue deficits, to provide blood/nutritional support to different cell/tissue types placed adjacent to or inside the host tissue filled tissue deficits, e.g., islet, epithelial, kidney, liver, etc., and to define the origin of such macro/microvasculature and to support the transplantation of the generated tissue to other locations in the patient for therapeutic or tissue restorative functions by reconnecting to the vascular system via plastic surgery and/or microsurgical techniques.

The tissue grafts of the present invention may be used for tissue repair, regeneration and reconstruction. They can be used as a repair or replacement device or as a surgical mesh to support soft tissue throughout the human body. The tissue grafts can be used as a skin wound dressing or a skin replacement tissue. They can also be used for hernia repair, colon, rectal, vaginal and or urethral prolapse treatment; pelvic floor reconstruction; muscle flap reinforcement; lung tissue support; rotator cuff repair or replacement; periosteum replacement; dura repair and replacement; pericardial membrane repair; soft tissue augmentation; intervertebral disk repair; and periodontal repair. The tissue grafts may also be used as a urethral sling, laminectomy barrier, or spinal fusion device. They may also serve as a carrier of bioactive agents, such as growth factors, to generate tissue.

The tissue graft of the present invention may be applied on a patient in need of tissue repair, regeneration or reconstruction. The small perforations in the tissue graft facilitates revascularization and cell repopulation in the patient. The large perforations allow fluid drainage. The large perforations reduce the occurrence of clotting and granulation tissue development within the perforations so that surgical drains or negative pressure wound therapy can be applied to remove extravascular tissue fluids from the implant site in the perioperative and early postoperative period.

EXAMPLES

Experimental results show that perforations of different sizes result in different host responses.

Example 1

Experimental results in hernia repair and intra-abdominal models showed that perforations above and below a particular size resulted in different host responses. The experiments were done on SURGIMEND Collagen Matrix (TEI Biosciences, Inc., Waltham, Mass.), which is derived from fetal or neonatal bovine dermis.

Smaller perforations (<3 mm diameter in 2 mm thick SURGIMEND matrix) are filled with newly deposited host connective tissue; this new connective tissue serves as a source of repopulating cells/vessels thereby increasing the rate of cell repopulation/revascularization of the surrounding implanted SURGIMEND extracellular matrix.

Larger perforations (>3 mm diameter in 2 mm thick SURGIMEND matrix) tended to stay open/empty of newly deposited host connective tissue.

Example 2

Experimental results in an intramuscular implant model showed that perforations above and below a particular size result in different host responses.

Smaller perforations (<3 mm diameter in 2 mm thick SURGIMEND matrix) are filled with newly deposited host connective tissue; this new connective tissue serves as a source of repopulating cells/vessels thereby increasing the rate of cell repopulation/revascularization of the surrounding implanted SURGIMEND extracellular matrix.

Larger perforations (>3 mm diameter in 2 mm thick SURGIMEND matrix) were large enough that muscle tissue could press into the pore, filling the pore with muscle tissue.

Figure 2:
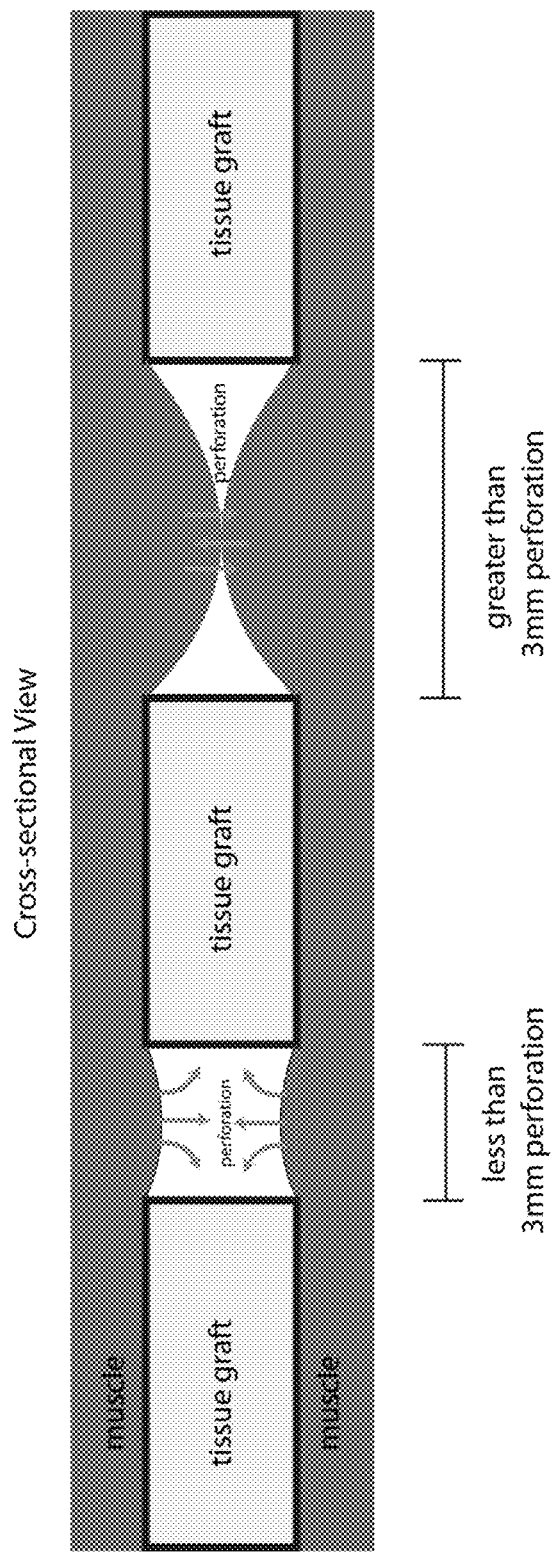
FIG. 2 is a schematic diagram and visual representation of perforations above and below the size threshold.

A schematic diagram and visual representation of perforations above and below the size threshold is provided in FIG. 2.

Example 3

The introduction of void spaces in decellularized tissue products modulates the biologic properties of the implant. More specifically, the size of the void spaces or holes affects the revascularization, tissue generation, and tissue remodeling characteristics whereby voids above and below a critical size result in different host responses. This response may vary based on the implant location and environmental signaling, but generally speaking smaller voids (<3 mm wide in 2 mm thick material) tend to be more rapidly revascularized and filled with newly deposited host tissue. Larger voids (>3 mm wide in 2 mm thick material) tend to stay open/empty of newly deposited host tissue.

TABLE 1

| Implant Environment Mechanical Constraint | Void Volume | |
|---|---|---|
| | <14.14 mm$^3$ | >14.14 mm$^3$ |
| Unconstrained | Void filled with newly deposited, cell dense host tissue, void contracted in size but not overall implant | remained open, increased fluid egress across the device |
| Uniaxial constraint | collapsed to slits | remained open |
| 3 dimensional constraint | Void filled with newly deposited, cell dense host tissue, void contracted in size but not overall implant | Void closed with existing tissue from above and below compressed into the space |

The invention may be embodied in other forms without departure from the scope and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

What is claimed is:

1. A tissue graft comprising:
   a sheet of a tissue graft material having a plurality of rows of small perforations, which pass through the sheet, and a plurality of rows of large perforations, which pass through the sheet;
   wherein the small perforations are smaller in size than the large perforations;
   wherein the small perforations have a diameter that is less than 3 mm and the large perforations have a diameter that is greater than 3 mm;
   wherein the diameters of the small perforations and the large perforations are in a ratio of about 1:1.2 to about 1:2.0;
   wherein the tissue graft has a thickness in a range of about 2 mm;
   wherein the tissue graft material is acellular animal dermis;
   wherein the rows of small perforations are substantially parallel to the rows of large perforations; and
   wherein the rows of small perforations alternate with the rows of large perforations, such that one small perforation is centered about every four adjacent large perforations, which are arranged in a substantially square or rectangular manner about the one small perforation, and one large perforation is centered about every four adjacent small perforations, which are arranged in a substantially square or rectangular manner about the one large perforation.

2. The tissue graft of claim 1, wherein the small and large perforations are substantially circular.

3. The tissue graft of claim 1, wherein the small perforations and the large perforations have open areas in a ratio of about 1:1.5 to about 1:3.

4. The tissue graft of claim 1, wherein the small perforations are sized to facilitate fibrin provisional matrix formation and granulation tissue development within the small perforations which, in turn, is a source of blood vessels and cells to facilitate revascularization and cell repopulation of the tissue graft implanted on the mammal.

5. The tissue graft of claim 1, wherein the large perforations are sized to reduce an occurrence of fibrin provisional matrix formation and granulation tissue development within the large perforations so that extravascular tissue fluids accumulating at an implant site in the mammal can readily drain through the tissue graft and be removed from the implant site in a perioperative and early postoperative period via surgical drains or negative pressure wound therapy.

6. The tissue graft of claim 1, wherein the large perforations are sized to enhance mammal tissue anchoring by permitting mammal tissue to compress into the large perforations increasing mammal tissue contact area.

7. The tissue graft of claim 1, wherein the large perforations and small perforations are distributed in staggered rows and columns.

8. The tissue graft of claim 1, wherein the plurality of rows of small and large perforations are equally spaced substantially on an entire surface of the tissue graft.

9. The tissue graft of claim 1, wherein the small perforations are spaced about 5 mm to about 20 mm apart and the large perforations are spaced about 5 mm to about 20 mm apart, as measured between centers of two adjacent perforations.

10. The tissue graft of claim 1, wherein the rows of small perforations and the rows of large perforations are spaced about 5 mm to about 20 mm apart.

11. The tissue graft of claim 1, wherein the tissue graft material is a biopolymer-based matrix produced from animal tissue.

12. The tissue graft of claim 1, wherein the tissue graft material is an acellular collagen matrix derived from fetal or neonatal bovine dermis.

13. The tissue graft of claim 1, wherein the small and large perforations that pass through the sheet are mechanically formed.

14. The tissue graft of claim 1, wherein the diameter of the small perforations is about 2 mm.

15. The tissue graft of claim 14, wherein the small perforations are spaced apart from each other by about 7 mm to about 15 mm and the large perforations are spaced apart from each other by about 7 mm to about 15 mm, as measured between centers of two adjacent perforations.

16. The tissue graft of claim 15, wherein the large perforations and small perforations are distributed in staggered rows and columns.

17. A method of repairing or constructing tissue in a patient, comprising:
providing a tissue graft comprising:
a sheet of a tissue graft material and having a plurality of small perforations, which pass through the sheet, and a plurality of large perforations, which pass through the sheet;
wherein the small perforations are smaller in size than the large perforations;
wherein the small perforations have a diameter that is less than 3 mm and the large perforations have a diameter that is greater than 3 mm;
wherein the diameters of the small perforations and the large perforations are in a ratio of about 1:1.2 to about 1:2.0;
wherein the tissue graft has a thickness in a range of about 2 mm;
wherein the tissue graft material is acellular animal dermis;
wherein the rows of small perforations are substantially parallel to the rows of large perforations;
wherein the rows of small perforations alternate with the rows of large perforations, such that one small perforation is centered about every four adjacent large perforations, which are arranged in a substantially square or rectangular manner about the one small perforation, and one large perforation is centered about every four adjacent small perforations, which are arranged in a substantially square or rectangular manner about the one large perforation;
applying the tissue graft to the patient at an implant site; and
allowing revascularization and cell repopulation in the patient.

18. The method of claim 17, comprising anchoring the tissue graft by compressing tissue into the large perforations, thereby increasing tissue contact area of the tissue graft.

19. The method of claim 17, comprising anchoring the tissue graft by compressing tissue into the large perforations from above and below the tissue graft.

20. The method of claim 17, wherein the large perforations are devoid of newly deposited host tissue.

21. The method of claim 17, comprising inducing clotting and granulation tissue development within the small perforations.

22. The method of claim 17, comprising:
anchoring the tissue graft by compressing tissue into the large perforations from above and below the tissue graft;
inducing clotting and granulation tissue development within the small perforation; and
draining extravascular tissue fluids that accumulate at the implant site through the large perforations;
wherein clotting and granulation tissue development within the large perforations is reduced compared to the small perforations.

23. The method of claim 17, comprising applying a surgical drain or negative pressure wound therapy to the implant site to remove extravascular tissue fluids from the implant site.

* * * * *